US00PP23387P3

(12) United States Plant Patent
Dirr

(10) Patent No.: US PP23,387 P3
(45) Date of Patent: Feb. 12, 2013

(54) ***HYDRANGEA PANICULATA* PLANT NAMED 'PIIHP-I'**

(50) Latin Name: *Hydrangea paniculata*
Varietal Denomination: PIIHP-I

(75) Inventor: Michael Dirr, Bogart, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 100 days.

(21) Appl. No.: 12/932,800

(22) Filed: Mar. 7, 2011

(65) Prior Publication Data

US 2012/0233731 P1 Sep. 13, 2012

(51) Int. Cl.
*A01H 5/00* (2006.01)

(52) U.S. Cl. ..... Plt./250
(58) Field of Classification Search ..... Plt./250
See application file for complete search history.

(56) References Cited

U.S. PATENT DOCUMENTS

PP19,082 P3 8/2008 Dirr

OTHER PUBLICATIONS

Page from Plant Introductions, Inc. website describing "*Hydrangea paniculata*-24" now known as "*Hydrangea paniculata* 'PIIHP-I'" downloaded Mar. 11, 2011.

*Primary Examiner* — June Hwu
(74) *Attorney, Agent, or Firm* — Greenlee Sullivan P.C.

(57) ABSTRACT

A new and distinct cultivar of *Hydrangea paniculata* plant named 'PIIHP-I', characterized by its compact rounded growth habit; strong stems that hold the inflorescences upright and do not splay; thick, dark green foliage; and solid inflorescences in which the showy white sepals cover the fertile flowers.

2 Drawing Sheets

Genus and species of plant claimed: *Hydrangea paniculata.*

Variety denomination: 'PIIHP-I'.

BACKGROUND OF THE INVENTION

The present invention relates to a new and distinct cultivar of *Hydrangea paniculata*, a member of the Hydrangeaceae family, hereinafter referred to by its cultivar name 'PIIHP-I'. 'PIIHP-I' is grown primarily as an ornamental for landscape use and for use as a potted plant.

'PIIHP-I' originated as an open-pollinated seedling from seed collected from *Hydrangea paniculata* 'HYPMAD I' (U.S. Plant Pat. No. 19,082) growing in Watkinsville, Ga. 'PIIHP-I' was selected in the summer of 2006 by the inventor in a cultivated environment in Dearing, Ga. from the progeny of this open-pollination by continued evaluation for growth habit and foliage and flower characteristics.

Asexual reproduction of 'PIIHP-I' by softwood cuttings since 2006 in Watkinsville, Ga. has shown that all the unique features of 'PIIHP-I', as herein described, are stable and reproduced true-to-type through successive generations of such asexual propagation.

SUMMARY OF THE INVENTION

Plants of the new cultivar 'PIIHP-I' have not been observed under all possible environmental conditions. The phenotype may vary somewhat with changes in light, temperature, soil and rainfall without, however, any variance in genotype.

The following traits have been repeatedly observed and are determined to be unique characteristics of 'PIIHP-I'. These characteristics in combination distinguish 'PIIHP-I' as a new and distinct cultivar: 1) Compact rounded growth habit. 2) Strong stems that hold the inflorescences upright and do not splay. 3) Thick, dark green foliage. 4) Solid inflorescences in which the showy white sepals cover the fertile flowers.

Plants of the new cultivar 'PIIHP-I' differ from plants of its female parent 'HYPMAD I' primarily in growth habit, stem strength, and foliage and flower characteristics, as plants of 'PIIHP-I' have a smaller, more compact growth habit, stronger stems, thicker, darker green foliage, and more dense inflorescences, whereas plants of the 'HYPMAD I' have a larger, less compact growth habit, weaker stems, lighter green foliage, and less dense inflorescences.

'PIIHP-I' can be compared to 'ILVOBO' (U.S. Plant Pat. No. 22,782) but differs in that 'PIIHP-I' has a rounded growth habit, begins flowering in late July, sepals age to green with reddish tinges, and inflorescences are smaller 13 cm×13 cm panicles. 'ILVOBO' has an upright and mounded growth habit, begins flowering in early July, sepals age to red-purple, and inflorescences are larger 27 cm×16 cm panicles.

'PIIHP-I' can also be compared to 'Jane' (U.S. Plant Pat. No. 22,330) but differs in that 'PIIHP-I' has a rounded growth habit, sepals begin white and age to green with reddish tinges, and inflorescences are true panicles. 'Jane' has an upright and mounded growth habit, sepals begin green and age to greyed purple, and inflorescences are rounded, mophead shaped panicles.

BRIEF DESCRIPTION OF THE DRAWINGS

The accompanying color photographs illustrate the flower and foliage characteristics and the overall appearance of 'PIIHP-I', showing the color as true as it is reasonably possible to obtain in color reproductions of this type. The photographs are of plants that are approximately 3 years old. Colors in the photographs may differ slightly from the color values cited in the detailed botanical description which accurately describe the colors of 'PIIHP-I'.

DETAILED DESCRIPTION

Figure 1:
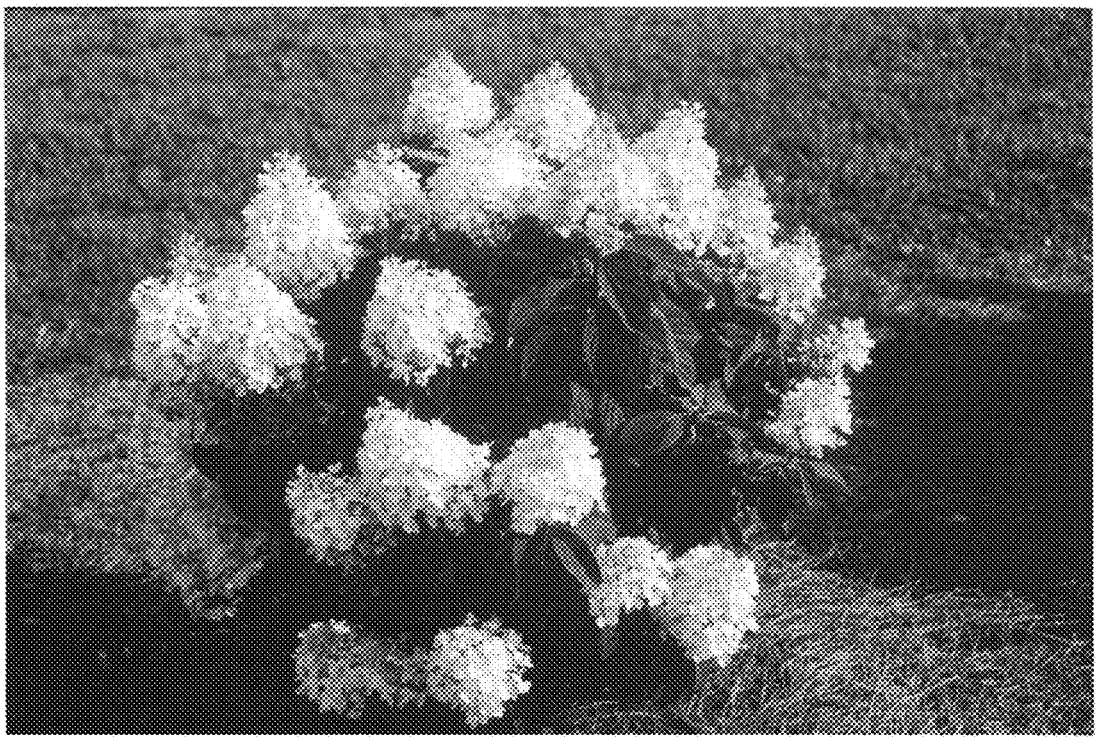
FIG. 1 illustrates the overall appearance and growth habit of 'PIIHP-I'.
Figure 2:
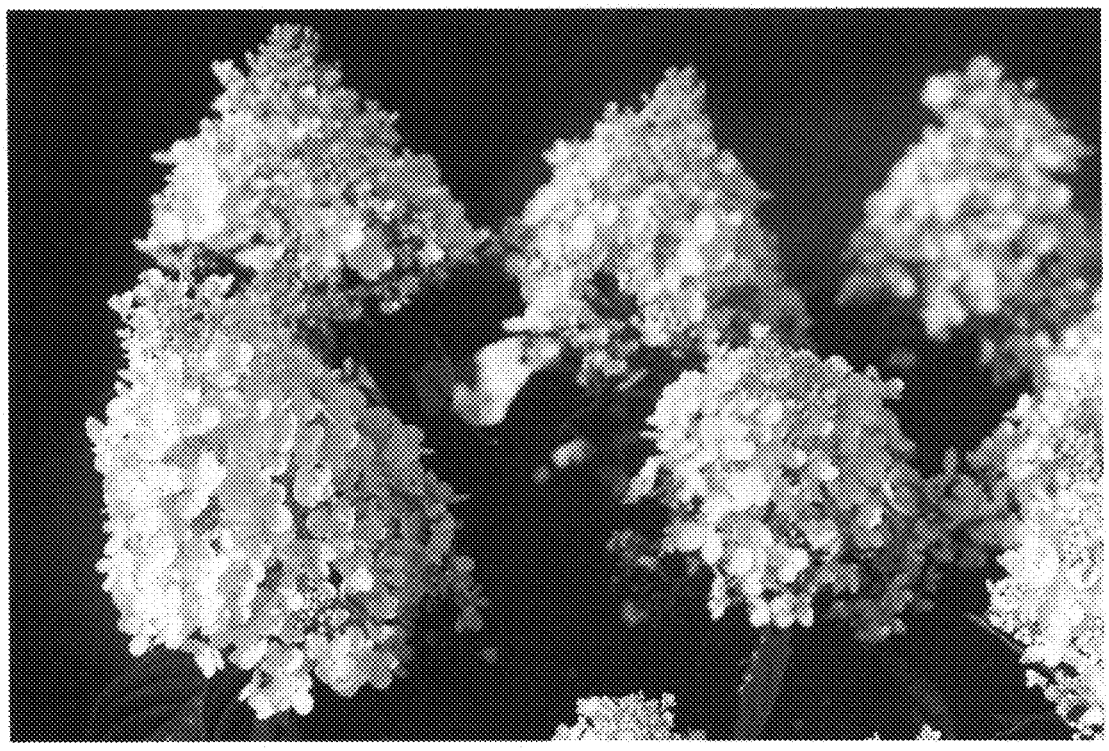
FIG. 2 illustrates a close-up view of the inflorescence of 'PIIHP-I'.

In the following description, color references are made to The Royal Horticultural Society Colour Chart, 2001 Edition, except where general terms of ordinary dictionary significance are used. Plants used for the description were approximately 3 years old and were grown in 11.8 L containers under outdoor conditions in Watkinsville, Ga.

Botanical classification: *Hydrangea paniculata*, cultivar 'PIIHP-I'.

Parentage: female, or seed, parent *Hydrangea paniculata* 'HYPMAD I' (U.S. Plant Pat. No. 19,082), male, or pollen, parent unknown (open-pollinated).

Propagation: Vegetatively by stem cuttings.

Time to initiate roots in summer: About 21 days at 32° C.

Plant description: Deciduous flowering shrub; multi-stemmed; compact rounded growth habit. Freely branching; removal of the terminal bud enhances lateral branch development.

*Root description*.—Medium, well-branched.

*Plant size*.—The original plant, now about 5 years-old in the ground, is about 122 cm high from the soil level to the top of the inflorescences and about 122 cm wide.

*First year stems*.—Have a diameter of about 5 mm. Shape: round. Pubescence: few coarse hairs. Exfoliation: none.

*First year stem color*.—145B when young and N199B when mature.

*Second year and older stems*.—Have a diameter of about 6 mm or more. Shape: round to oval. Lenticels: approximately 5 per cm of stem length, about 1 mm in diameter and N199C in color.

*Second year and older stem color*.—197B.

*Stem strength*.—Somewhat flexible when young becoming more easily broken as they mature.

*Internode length*.—About 3 cm.

*Trunk diameter*.—About 1.5 cm at the soil line.

*Color*.—197B.

*Lenticels*.—Approximately 10 per cm of stem length, about 2 mm in length, about 1 mm in width, and 200D in color.

The surface texture of young, first year stems is smooth, while older stems and the trunk have a rough surface texture.

Vegetative bud description:

*Arrangement*.—Opposite.

*Shape*.—Imbricate, rounded to globose.

*Size*.—About 1 mm in length, about 1 mm in width.

*Color*.—200D.

Foliage description:

*Arrangement*.—Opposite, simple.

*Length*.—About 8.5 cm.

*Width*.—About 4.5 cm.

*Shape*.—Ovate.

*Apex*.—Acute.

*Base*.—Acute.

*Margin*.—Finely serrate.

*Texture* (*upper and lower surfaces*).—Thick, pubescent, like fine sandpaper.

*Venation pattern*.—Pinnate.

*Venation color* (*upper and lower surfaces*).—145C.

*Color of emerging foliage*.—144A on the upper surface and 145B on the lower surface.

*Color of mature foliage*.—137A on the upper surface and 138B on the lower surface.

*Color of foliage in fall* (*upper and lower surfaces*).—3C.

*Petiole length*.—About 1.2 cm.

*Petiole diameter*.—About 2 mm.

*Petiole texture*.—Pubescent.

*Petiole color* (*upper and lower surfaces*).—145B.

Flower description:

*Flower type and arrangement*.—Inflorescence is a panicle about 13 cm in diameter and about 13 cm high. An inflorescence contains about 250 individual sterile flowers and about 350 individual fertile flowers. Inflorescence bloom period: Summer, usually late July in Watkinsville, Ga. The sterile flowers retain their color and are showy for about 6 weeks. The sterile flowers have showy sepals but no petals or reproductive organs. The fertile flowers are mostly hidden by the sterile flowers and are not showy. The fertile flowers have petals and reproductive organs but no sepals. The peduncle is about 10 cm long, 3 mm wide, finely setose, and 155B in color.

Fertile flowers:

*Flower bud length*.—About 3 mm.

*Flower bud diameter*. —About 2 mm.

*Flower bud shape*.—Round. Color: 155C.

*Flower diameter*.—About 7 mm.

*Flower height*.—About 5 mm. The fertile flowers within an inflorescence open over a period of one to two weeks and are persistent on the plants.

*Pedicels*.—About 2 mm in length, about 1 mm in width, finely setose, and 155B in color.

*Petals*.—5 petals per flower.

*Petal length*.—About 3 mm.

*Petal width*.—About 2 mm.

*Petal shape and texture*.—Elliptical, with acute apex, cuneate base, and entire margin.

*Texture of upper and lower surfaces*.—Smooth with no pubescence.

*Petal color*.—At peak of bloom the upper and lower surfaces of the petals are 155A.

*Stamens*.—Quantity: usually 10 per flower. Anthers: about 1 mm in length and about 1 mm in width, and 197C in color. Filaments: about 2.5 mm in length and about 0.5 mm in width, and 155A in color. Pollen: produced in very small quantities per flower (scarce), and 155B in color.

*Pistils*.—Quantity/arrangement: 1 per flower, superior, globose in shape. Pistil length: about 3 mm. Pistil width: about 2 mm. Pistil color: 160C. Stigma: 3 per pistil, round in shape and 158A in color. Style: about 2 mm in length, columnar in shape, and 158A in color. Ovary: 1 per flower, about 1 mm in height and width, round in shape, and 158A in color.

Sterile flowers:

*Flower diameter*.—About 1.8 cm. The sterile flowers within an inflorescence open over a period of about one to two weeks and are persistent on the plant.

*Pedicels*.—About 1.3 cm in length, about 1 mm in width, finely setose, and 155B in color.

*Sepals*.—3 to 5 (usually 4) sepals per flower.

*Sepal length*.—About 1 cm.

*Sepal width*.—About 8 mm.

*Sepal shape and texture*.—Broad elliptical with obtuse to rounded apex, acute to rounded base, and entire margin.

*Texture of upper and lower surfaces*.—Smooth with no pubescence.

*Sepal color*.—Upper and lower surfaces are 157D at peak bloom and age to 145B with tinges of 51D.

Fruit:

*Type and shape*.—The fruit is a persistent dehiscent capsule, ovoid in shape.

*Length*.—About 4 mm.

*Width*.—About 2 mm.

*Color*.—N199C at maturity.

*Quantity*.—About 350 or more per infructescence.

*Seeds*.—Linear in shape, about 2 mm in length and about 1 mm in width, N199D in color, and each capsule contains about 50 or more seeds.

Disease/pest resistance: Plants of the claimed *Hydrangea* cultivar grown in the garden have not been noted to be susceptible to pathogens and pests common to *Hydrangea*.

Weather and temperature tolerance: Plants of the new *hydrangea* have been observed to be cold hardy in USDA Hardiness Zones 4-8.

I claim:

1. A new and distinct *Hydrangea paniculata* plant named 'PIIHP-I', substantially as illustrated and described herein.

* * * * *